(12) United States Patent
Steinmetz

(10) Patent No.: US 8,648,716 B2
(45) Date of Patent: Feb. 11, 2014

(54) APPARATUS, METHOD, DEVICE AND COMPUTER PROGRAM PRODUCT FOR AUDIBLY COMMUNICATING MEDICINE IDENTITY, DOSAGE AND INTAKE INSTRUCTION

(75) Inventor: Jay Steinmetz, Baltimore, MD (US)

(73) Assignee: Barcoding, Inc., Baltimore, MD (US)

( * ) Notice: Subject to any disclaimer, the term of this patent is extended or adjusted under 35 U.S.C. 154(b) by 0 days.

(21) Appl. No.: 13/331,556

(22) Filed: Dec. 20, 2011

(65) Prior Publication Data

US 2012/0183941 A1 Jul. 19, 2012

Related U.S. Application Data

(63) Continuation-in-part of application No. 12/431,761, filed on Apr. 29, 2009, now abandoned, which is a continuation of application No. 11/523,464, filed on Sep. 15, 2006, now abandoned.

(60) Provisional application No. 60/724,280, filed on Oct. 7, 2005.

(51) Int. Cl.
*G08B 1/08* (2006.01)
(52) U.S. Cl.
USPC ............... 340/539.12; 340/573.1; 340/691.6

(58) Field of Classification Search
USPC ............. 340/539.12, 573.1, 691.6, 825.19
See application file for complete search history.

(56) References Cited

U.S. PATENT DOCUMENTS

| 2002/0017996 A1* | 2/2002 | Niemiec | 340/573.1 |
| 2003/0189089 A1* | 10/2003 | Raistrick et al. | 235/375 |
| 2005/0168337 A1* | 8/2005 | Mahoney | 340/539.12 |
| 2005/0237222 A1* | 10/2005 | Bogash et al. | 340/870.07 |

* cited by examiner

*Primary Examiner* — Steven Lim
*Assistant Examiner* — Hongmin Fan
(74) *Attorney, Agent, or Firm* — Hunter Clark PLLC

(57) ABSTRACT

A system for identifying medication in the form of pills, capsules or tablets, and communicating medicine dosage and intake instructions to a user, utilizing Radio Frequency Identification Devices (RFID) and optical recognition technology. The RFID is performed by labeling a medicine container with a tag containing a unique identifier, associating the unique identifier with an audio file comprising instructions related to medicine usage, and delivering the audio file to an electromagnetic wave-enabled device. A wireless device, such as a mobile telephone or PDA, via a service, plays an audio and/or vibrational file associated with the unique identifier when the RFID tag is read by the device. The mobile device has a camera therein and is operable to capture an image of the pill, capsule or tablet and, via execution of optical recognition software, identify the pill, tablet or capsule, and verify the identity thereof.

29 Claims, 4 Drawing Sheets

APPARATUS, METHOD, DEVICE AND COMPUTER PROGRAM PRODUCT FOR AUDIBLY COMMUNICATING MEDICINE IDENTITY, DOSAGE AND INTAKE INSTRUCTION

REFERENCE TO RELATED APPLICATION

The present application is a CIP (continuation-in-part) patent application of co-pending application Ser. No. 12/431,761, filed Apr. 29, 2009, the contents of which are incorporated herein by reference.

FIELD OF THE INVENTION

The present invention provides a system for identifying medicine in the form of pills, tablets or capsules, and communicating dosage and intake instructions thereof to a patient via an RFID-enabled mobile device. In particular, a system is provided for identifying medicine in the form of pills, tablets or capsules, via interrogation of an RFID tag associated with the pills, tablets or capsules, and/or preferably via optical recognition techniques, as well as storage compliance, and communicating dosage and intake instructions, as well as identification and medicine stability, thereof to a patient via an RFID-enabled mobile device.

BACKGROUND OF THE INVENTION

Improving medication compliance is a universal healthcare goal in patient care. However, the process of ensuring medicament compliance is an ongoing struggle that requires strict adherence to a routine dosage regime. Difficulties in managing daily medication regime may be exacerbated by age and physical disabilities, such as visual impairment. The vast majority of individuals who generally have medication compliance and adherence problems due to visual impairments are elderly patients. Visual impairment typically exacerbates the difficulties in explaining medication regimens to this patient population, thus resulting in non-compliance or self-care error. In some instances, the elderly, blind or visually impaired face severe and sometimes dangerous challenges in managing their own self-care and medication schedule.

According to the American Foundation for the Blind, estimates of the number of people with difficulty seeing (even when using one's usual eyeglasses) range from as low as 7 million to as high as 20 million people (all ages). There is greater consistency in estimates of the number of people with very severe visual impairment, which is estimated as approximately 1.5 million to 2 million people. When used correctly, prescribed medications have the potential of greatly improving the health and independence of individuals who are blind or visually impaired.

Access to drug information, including drug labels and usage instructions, is an important component to improving medication compliance. As the number of prescribed or recommended medications and/or vitamins and supplements increases for any individual patient, the difficulty in managing the proper dosing regime also increases. Prescriptions differ in quantity, daily dosages and other requirements, such as a medication requiring concurrent food intake. As a patient's need for drug information increases, so to does their need for assistance in the management of their intake regimes. In most cases, blind or visually-impaired individuals are generally assisted by a caregiver, who instructs these individuals on how to take their medications and other counseling information provided by the pharmacists and doctors.

In the absence of a caregiver, providing drug information to the visually impaired population is practically challenging. A number of medication compliance systems have been developed that attempt to address the challenge assisting visually impaired patients in managing their daily regime of prescription drugs, vitamins, etc. Some solutions do not account for the capabilities of the majority of the patient population. For instance, products available in Braille are not useful to older Americans who may not have developed visual impairment issues until later in life, and thus, never learned Braille. For example, macular degeneration is a common problem among millions of Americans 65 or older.

In order to deal with the problem of providing drug information to the visually impaired patients, a number of non-technical measures are employed. Most often, the visually impaired patient population must rely on verbal counseling from a caregiver, pharmacist or doctor for the proper instruction. Where visual impairment is not yet severe, a magnifying glass may be employed to identity the appropriate medication for purchase or for self-administration. Additionally, patients try themselves to overcome their disability by trying to memorize the shape of the pill, and the way it feels in their hands, because the print is too small and all the bottles are of similar size and shape. The chances of error are great where those living alone must often rely on the memory, reading skills, and good graces of the next visitor to help them if they become confused by the passage of time and the need to memorize other information.

Technological measures have also been employed to address this problem. For example, alarms and beepers are used to remind a patient when it is time to medicate. The main problem with conventional drug compliance devices is a lack of real time interactivity from the patient, the patient's doctor and the pharmacist, with regard to the patient's drug compliance.

Another problem with conventional drug compliance devices is that the devices are not wireless, hence they are not portable, and require the patient's active input to operate. Or, if they are wireless, they require specialized dispensing containers, and cannot identify medication not previously identified and properly placed within the specialized container. For example, U.S. Patent Application Publication No. 2004/0155780 A1, to Rapchak, et al., discloses a medication compliance system for dispensing medication to a patient. This Rapchak, et al. system is comprised generally of a dispensing unit 16, a cell phone 14, and a host 20, as illustrated in FIGS. 1 and 2. As illustrated in FIGS. 1-3, the Rapchak, et al. system physically controls the dispensing of medication 116. In particular, the "dispenser is remotely controlled by the host 20" (see paragraph [0027]). Thus, the Rapchak, et al. system requires a remotely controlled dispensing unit 16, limiting the scope and availability of the system, and preventing the use of current medication containers dispensed regularly in pharmacies.

In another example described in U.S. Patent Publication No. 2006/0079996 A1, to Benouali, a unit dosage monitoring and reporting device and system is provided, which again include a specialized "dispenser shell formed with dose compartments". As clearly illustrated in FIGS. 1-6, the medicine is prepackaged in the specialized dispenser shell of Benouali, and is dispensed via wireless command. However, as with the system of Rapchak, et al., described above, the prior system of Benouali is unable to identify medicine in the forms of pills or capsules that are not prepackaged within the dispenser, and is unable to be utilized with conventional medicine containers.

A final problem with conventional drug compliance devices is that they are expensive and the cost for the device is borne by the patient/consumer. As discussed in detail above, the conventional medicine dispensing and compliance systems generally require specialized dispensers, which are usually both expensive and not easily obtainable. Further, these dispensers must generally be loaded with a users medicine, which requires a user to arrange for same, a difficult task.

In order to overcome the above disadvantages associated with these conventional systems, it is the object of the present invention to provide a practical system for communicating medicine dosage and intake instructions to patient utilizing a device that is equipped the radio frequency identification (RFID) capabilities, such that the RFID capabilities enables the user to identify the proper medicine and triggers audible instructions for use of that medicine to play for the user.

The inventors of the present invention have recognized that by providing radio frequency identification (RFID) enabled mobile devices, such as mobile phones, new markets can be developed that heretofore have been untapped by the wireless communications industry. As one example, the present invention was developed utilizing typical consumer product mobile phones as a platform for RFID technology.

It is another object of the present invention to permit visually-impaired patients to identify medication and receive dosage and intake instructions via RFID enabled mobile phones. Conventional systems are generally unable to provide It is a further object of the present invention to assist patient populations that are typically non-compliant with regard to medication regimes due to some other physical or mental ailment, such as memory loss or Alzheimer's, to become compliant with their dosing regime by monitoring their dosage and providing verbal warnings/instructions concerning same.

It is final object of the present invention to provide a wireless system for communicating medicine dosage and intake instructions to patients utilizing conventional medicine containers, with RFID tags attached thereto or in communication therewith, thus eliminating the need for specialized medication dispensers.

SUMMARY OF THE INVENTION

In order to achieve the objects of the present invention, as described above, the present invention provides, the present invention utilizes RFID-enabled network devices that run computer programs designed to identify medicine capsules or pills, and communicate the medicine's identity, dosage and intake instructions to a patient in need thereof, as well as monitor their intake thereof. In particular, in a first embodiment of the present invention, a system for identifying medicine, and communicating dosage and intake instructions thereof to a patient via an RFID-enabled mobile device is provided, the system comprising:

(a) one or more RFID tags having a unique identifier associated therewith in communication with and/or adjacent to one or more of a medicine and a medicine container, said medicine being in the form of pills and/or capsules;

(b) an RFID-enabled mobile device comprising a computer processor, a wireless communications means in communication with the computer processor, an RFID reader in communication with the computer processor, a camera in communication with the computer processor, and a non-transitory computer readable medium in communication with the computer processor; and (c) a subsystem operable to identify pills and capsules via optical recognition methods based on one or more of color, shape and size, associate one or more users with one or more pills and capsules, and transmit an audio file in the form of one or more of a ringtone, text message, voice message, vibration, and audio identification associated with the unique identifier embodied on an RFID tag comprising identity of medicine and instructions related to medicine usage via a network to the RFID-enabled mobile device, said subsystem comprising computer application program code embodied on the non-transitory computer readable medium executable by the processor, for identifying medicine, and communicating dosage and intake instructions thereof to a patient via an RFID-enabled mobile device, comprising:

(i) computer program code operable to generate, store and transmit a date stamp corresponding to the unique identifier when an RFID tag containing the unique identifier is read, and compare the date stamp to medicine dosage and intake instructions corresponding to a patient associated with the RFID-enabled mobile device, so as to determine compliance with the medicine dosage and intake instructions;

(ii) receive an image of a sample pill or capsule from the camera and/or processor, generate a data set of optical characteristics of the sample pill or capsule based on the image, and compare the data set of optical characteristics of the sample pill or capsule to a database of known optical characteristics of known pills and capsules, so as to determine identity of the sample pill or capsule;

(iii) compare the identified sample pill or capsule, medicine dosage and intake instructions to patient medicine identity, dosage and intake requirements, so as to determine compliance therewith;

(iv) cause a service to generate and play an audible alarm so as to inform the user of medicine dosage and intake requirements associated with the user, and record acknowledgement of the audible alarm by the user, so as to determine compliance with medicine dosage and intake instructions; and (v) cause a service to play an audio file on the RFID-enabled mobile device, said audio file comprising identity of the sample pill or capsule, and instructions related to dosage and intake thereof.

In a second embodiment of the present invention, the system of the first embodiment above is provided, further comprising:

(a) a temperature sensor in communication with the computer processor, said temperature sensor operable to record and transmit temperature data, (b) computer program code operable to receive temperature data from the temperature sensor, and compare recommended storage temperatures for the sample pills or capsules to the received temperature data so as to determine compliance with the recommended storage temperatures; and (c) computer program code operable to cause a service to play an audio file on the RFID-enabled mobile device, said audio file comprising notification of the compliance or non-compliance with recommended storage temperatures for the sample pills or capsules, and optionally time range out of recommended storage temperatures that damages or renders pills or capsules ineffective or dangerous for consumption.

In a third embodiment of the present invention, the system of the first embodiment above is provided, wherein the RFID-enabled mobile device is operable to communicate with an authorized mobile phone.

In a fourth embodiment of the present invention, the system of the first embodiment above is provided, wherein the RFID-enable mobile device is a mobile phone.

In a fifth embodiment of the present invention, the system of the first embodiment above is provided, further comprising:
 a gyroscopic detection device in communication with the computer processor, said gyroscopic detection device operable to detect the 3 dimensional orientation of the mobile device;
 computer program code operable to compare the detected 3 dimensional orientation of the mobile device to a predetermined proper orientation for the mobile device; and
 computer program code operable to cause a service to play an audio file on the RFID-enabled mobile device, said audio file comprising instructions concerning reorientation of the mobile device needed to correspond the detected orientation thereof to the predetermined proper orientation.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE INVENTION

Figure 1:
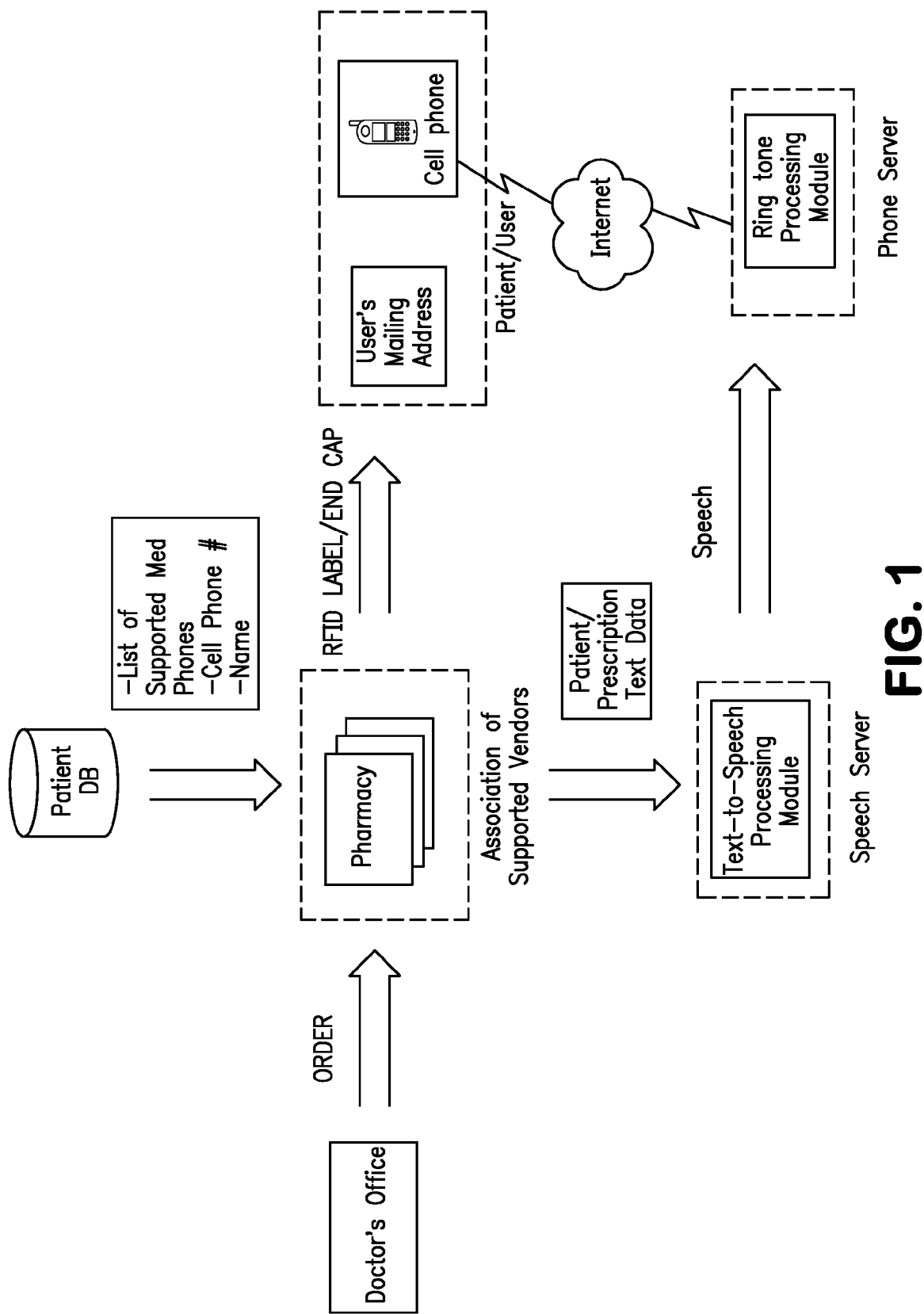
FIG. 1 is a block diagram of an example wireless communication network according to one embodiment of the invention where audio files are generated by a text to speech process module.
Figure 2:
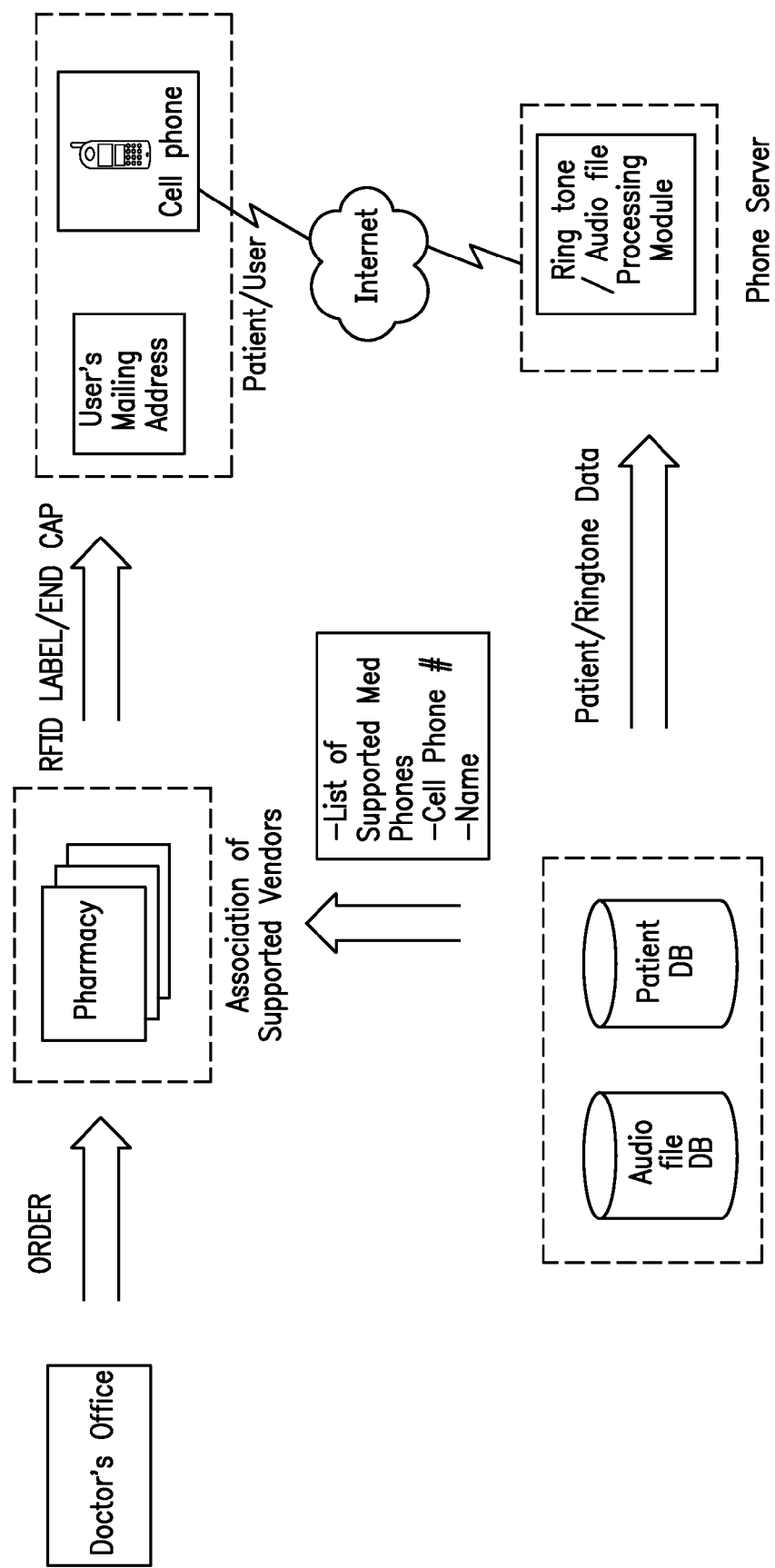
FIG. 2 is a block diagram of an example wireless communication network according to one embodiment of the invention where audio files are accessed from a database.
Figure 3:
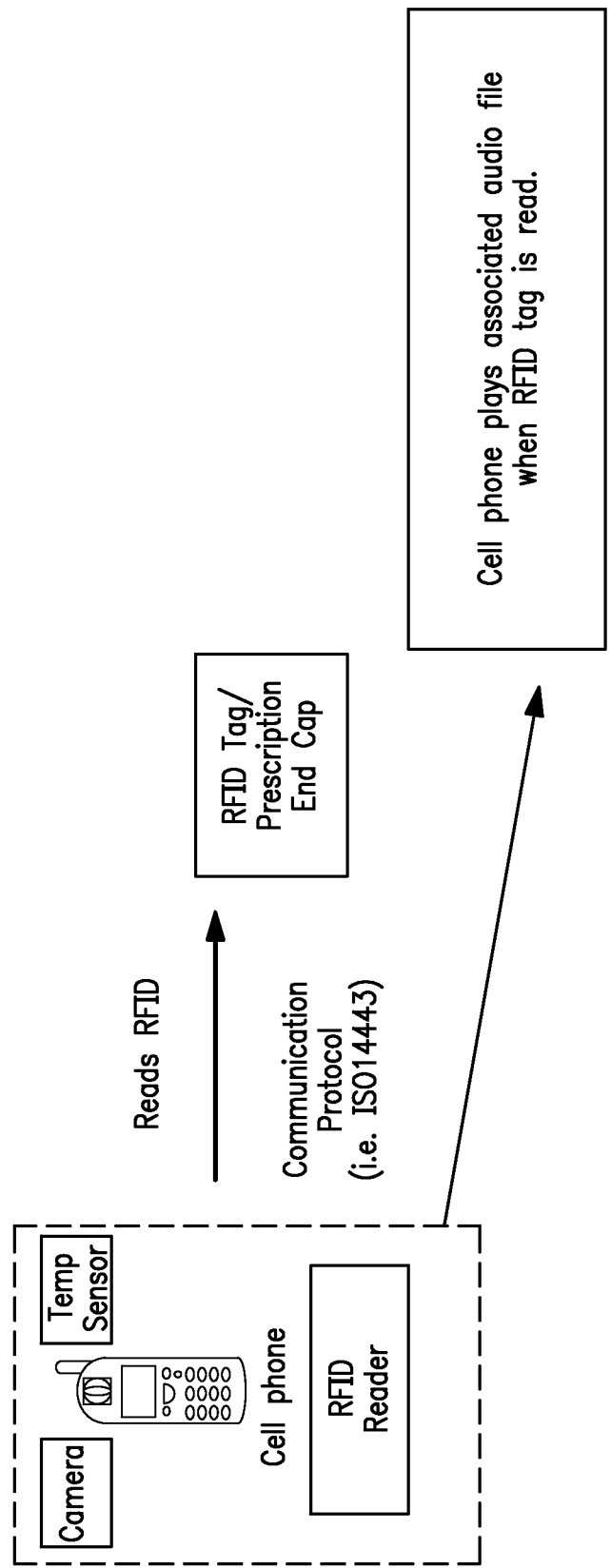
FIG. 3 is a block diagram of an example RFID-enabled mobile phone reading a RFID tag attached to a conventional medicine container.
Figure 4:
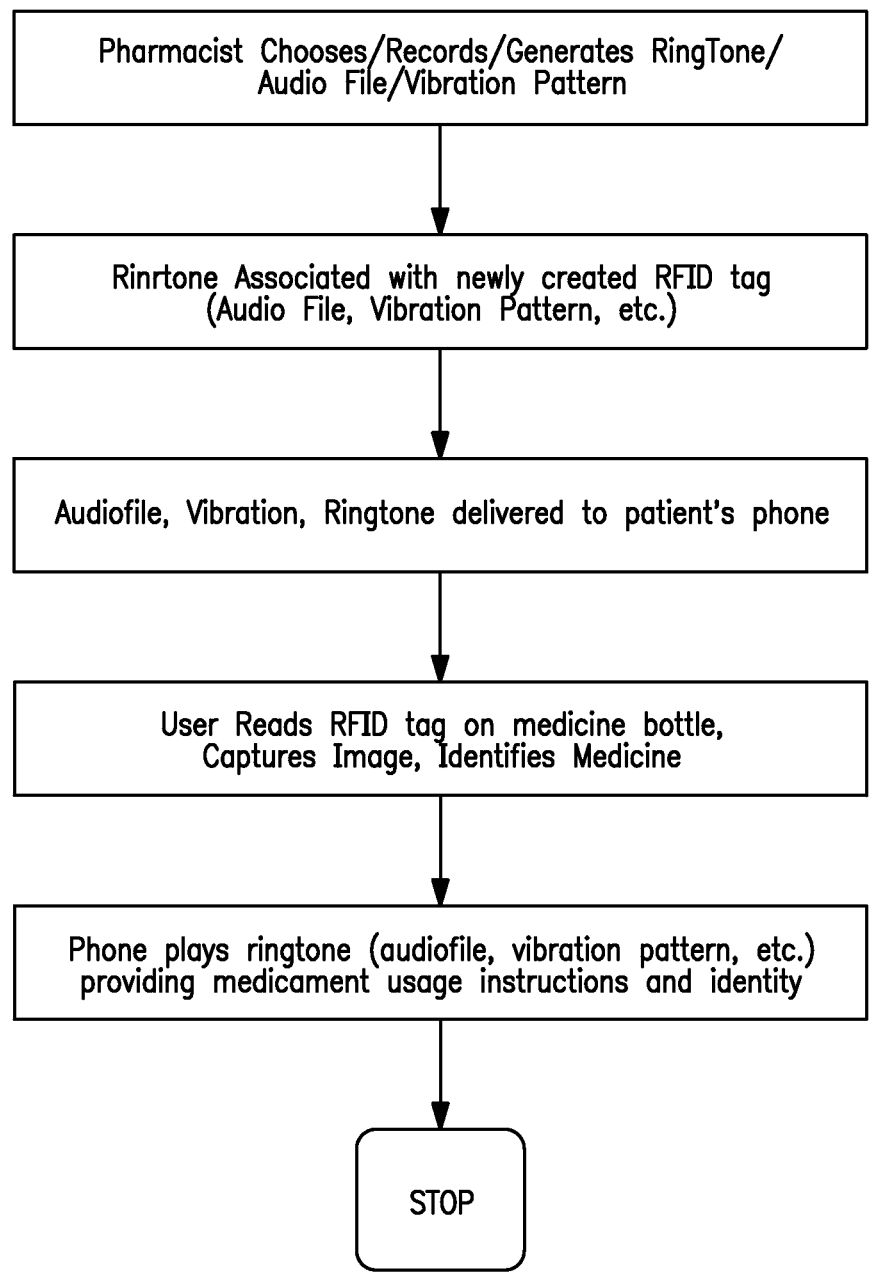
FIG. 4 is a flow chart illustrating an example of steps taken to deliver audio files to a RFID-enable device for communicating medicine identity, dosage and intake instructions to a patient.

As mentioned above, the present invention provides a system for identifying medicine, and communicating dosage and intake instructions thereof to a patient via a wireless networked device, such as an RFID-enabled mobile device. The wireless networked device of the present invention may be any wireless communication device such as a telephone, personal data assistant (PDA), pager, multi-function device, or other communication device. The RFID-enabled mobile device of the present invention, in order to carry out the functions desired herein, preferably comprises a computer processor, a wireless communications means in communication with the computer processor, an RFID reader in communication with the computer processor, a camera in communication with the computer processor, and a non-transitory computer readable medium in communication with the computer processor.

In a preferred embodiment of the present invention, the wireless networked device is a mobile phone, such as any common consumer mobile phone product equipped with a microprocessor. A mobile phone, also known as a cellphone or cellular phone, is a portable electronic device which behaves as a normal telephone whilst being able to move over a wide area (compare cordless phone which acts as a telephone only within a limited range). Cellphones allow connections to be made to the telephone network, normally by directly dialing the other party's number on an inbuilt keypad. Most current cellphones use a combination of radio wave transmission and conventional telephone circuit switching, though packet switching is already in use for some parts of the cellphone network, especially for services such as Internet access and WAP.

Wireless Application Protocol (WAP) is an open international standard for applications that use wireless communication, for example Internet access from a mobile phone. WAP was designed to provide services equivalent to a Web browser with some mobile-specific additions, being specifically designed to address the limitations of very small portable devices. It is now the protocol used by the majority of the world's mobile internet sites, otherwise known as wap-sites. The Japanese i-mode system is the other major competing wireless data protocol.

Whereas WAP represents one protocol in wireless communications, the application of the present invention may utilize any of the interfaces or protocols for wireless communications known to the relevant programming community. For example, short message service (SMS) is widely used for delivering to mobile devices premium content, such as ringtones. Other services include enhanced messaging service (EMS) messages, multimedia messaging service (MMS) messages, or other types of messages sent to and/or from wireless devices within the wireless communication network, including, but not limited to immediate messaging (IM) and presence services (IMPS), mobile e-mail, and Internet protocol (IP)-based multimedia service (IMS).

Wireless communications networks are described in more detail in Gralla, P., "How Wireless Works," Que, 2002, and in particular in Chapters 10 and 11 thereof, and in Le Bodic, G., "Mobile Messaging Technologies and Services: SMS, EMS and MMS," John Wiley & Sons, Ltd. 2003, and in particular in Chapter 1 thereof, the entire contents of all three of these chapters being incorporated herein by reference.

The system of the present invention further comprises one or more RFID tags having a unique identifier associated therewith in communication with and/or adjacent to one or more of a medicine and a medicine container, said medicine being in the form of pills and/or capsules. These RFID tags are conventional RFID tags now commonly utilized in many different industries. Preferably, the one or more RFID tags of the present invention are passive in nature, thereby eliminating the need for a power source in communication therewith, and minimizing the cost thereof.

A typical RFID solution consists of a tag and a reader. The reader, when activated, emits a short-range radio signal that powers up the tag, enabling the data on the tag to be read. The present invention utilizes an RFID-enabled networked device that can read information stored on RFID labels or tags. This functionality may be embedded in the networked mobile device or implemented as RFID reader shells. The RIFD reader shells acts as an input accessory for use with a networked device, which runs the software for tag reading. Each tag contains a specific serial number that the device links with initiation of a service. Where a device is a mobile phone, the initiated service may be a call, messaging, browsing or recording data.

The present invention utilizes devices that operate on a network. These networks include networks suitable for the transmission of digital information, which include, but are not limited to, wide area networks (WAN), personal area networks (PANs), metropolitan area networks (MANs), local area networks (LANs) or the public switched telephone network (PSTN).

Importantly, the system of the present invention further comprises a subsystem operable to identify pills and capsules via optical recognition methods based on one or more of color, shape and size, associate one or more users with one or more pills and capsules, and transmit an audio file in the form of a ringtone, text message and/or a voice message associated with the unique identifier embodied on an RFID tag comprising identity of medicine and instructions related to medicine usage via a network to the RFID-enabled mobile device. Specifically, in addition to simply identifying medicine by reading an RFID tag associated with the container from which the medicine is dispensed, the system of the present invention is operable to identify the pill or capsule itself by utilizing optical recognition technology, including the use of image capture hardware (i.e., a camera) in conjunction with optical recognition software.

For example, to verify the identity of the pill or capsule if the container is not equipped with an RFID tag, or to verify the accuracy of the RFID tag data, the user may capture an image of the pill or capsule, and utilize the system software to determine the identity of the pill or capsule by cross referencing a database of known pill or capsule characteristics. In particular, the system comprises computer application program code embodied on the non-transitory computer readable medium executable by the processor, for identifying medicine, and communicating dosage and intake instructions thereof to a patient via an RFID-enabled mobile device, comprising:

(i) computer program code operable to generate, store and transmit a date stamp corresponding to the unique identifier when an RFID tag containing the unique identifier is read, and compare the date stamp to medicine dosage and intake instructions corresponding to a patient associated with the RFID-enabled mobile device, so as to determine compliance with the medicine dosage and intake instructions;

(ii) receive an image of a sample pill or capsule from the camera and/or processor, generate a data set of optical characteristics of the sample pill or capsule based on the image, and compare the data set of optical characteristics of the sample pill or capsule to a database of known optical characteristics of known pills and capsules, so as to determine identity of the sample pill or capsule;

(iii) compare the identified sample pill or capsule, medicine dosage and intake instructions to patient medicine identity, dosage and intake requirements, so as to determine compliance therewith;

(iv) cause a service to generate and play an audible alarm so as to inform the user of medicine dosage and intake requirements associated with the user, and record acknowledgement of the audible alarm by the user, so as to determine compliance with medicine dosage and intake instructions; and (v) cause a service to play an audio file on the RFID-enabled mobile device, said audio file comprising identity of the sample pill or capsule, and instructions related to dosage and intake thereof.

According to a preferred embodiment of the present invention, preferably, a patient will receive their medication in containers that are labeled with an RFID tag. The location of the RFID tag on the container can be anywhere that suits the needs of the distributor of the medication. The RFID tags may be printed with the medicine label, or attached to the bottle or cap itself. When the patient desires or is required to take medication, the patient may use the RFID-enabled network device to read the RFID tag associated with the medicine. That event will then initiate execution of the computer program code described above, resulting in the initiation of an audio file stored on the RFID-enabled network device to play and communicate the dosage and intake instructions therein.

In one preferred embodiment, the audio file will play in the form of a ringtone. A ringtone is the sound typically made by a telephone and used to indicate an incoming call. The term is most often used to refer to the customizable sounds available on mobile phones. In the present invention, audio files are recorded and associated with medication as a means to communicate the identity, dosage and intake instructions for use. An RFID-enabled device communicates medicament instructions by initiating a ringtone mechanism to play the audio file when the RFID tag is read, not as an indication of an incoming call.

Ringtones of the present invention may be monophonic or polyphonic. The ringtones of the present invention may be contained in MP3, WMA, WAV, QCP, or AMR format, but are not limited to these formats.

In another preferred embodiment of the invention, the audio file plays through the earpiece of the mobile phone in the form of a voice message, or via the mobile device through the emission of a vibration or series of vibrations (which correspond to a predetermined message understandable by the user). Once the phone reads the RFID tag, the audio file begins to play through the earpiece of the phone, which the patient then listens to in the normal course of using the phone. Additional features may be added, such as permitting the user to repeat the instructions. That is, once the recording has ended, that caller is given the option of accessing the file or repeating the vibration/series of vibrations again by pressing a key on the keypad or other input source on the device.

The audio files may be created or generated utilizing a number of methods and additional technologies. These include, but are not limited to, simple voice recording and the conversion of text information to audio speech by an embedded text-to-speech processor. Examples of text-to-speech processors include TMS320C203 from Texas Instruments, V8600 from RC Systems, and MSM7630 from OKI Semiconductor.

The audio files may be stored in the database for retrieval by a user, such as a pharmacist, at the time the ringtone is associated with the RFID tag. Alternatively, the pharmacist may customize instructions at the time the prescriptions are filed. The pharmacist may make a voice recording or utilize other technology that permits the transformation of written text into speech. If not already, this generated audio file is then converted into a format suitable for use as a ringtone.

The ringtones or audio files of the present invention may be delivered to mobile phones in the normal course over wireless communication networks. Alternatively, equipping phones with Bluetooth (or other specification for wireless PAN) or PC-link up would permit users to transfer ringtones created on a PC (personal computer), to their phone.

WAP Push, available since WAP 1.2, has been incorporated into the specification to allow WAP content to be pushed to the mobile handset with minimum user intervention. A WAP Push is basically a specially encoded message which includes a link to a WAP address. In addition to SMS mentioned above, WAP Push represents another means by which to deliver content to wireless devices over a wireless network.

The operation of the wireless device is controlled by the microprocessor programmed with instructions that are stored in memory. The memory holds data that is accessible by application operating on the wireless device. For example, a mobile phone may store a phone book that can be maintained by the user. Software applications that are run by the microprocessor may access this data in memory. Those of ordinary skill in the art would understand that common applications for a wireless device, such as a mobile phone, are readily programmable.

In the present invention, an application running on a wireless device would respond to an RFID tag reading event. When a RFID tag is read, data, including a unique tag identifier such as a serial number, is transferred and captured by the wireless device. In one embodiment of the present invention, that unique tag identifier is assigned to a ringtone that is then played by the wireless device. By recognizing the unique tag identifier, a simple comparison is made in a database to determine if an entry exists for that particular tag, and if so, which ringtone has been assigned to it. If there has been such an assignment, the selected ringtone is played. If not, a default message corresponding to a particular event is played.

Another concern with medication is proper storage temperature. Frequently, medicine requires storage within a certain temperature to ensure prevention of degradation or spoilage thereof. In another preferred embodiment of the present invention, the system is operable to determine whether the medicine to be taken by the patient has been stored at proper temperature. To achieve same, a temperature sensor is provided in communication with the computer processor of the mobile device, as well as computer program code executable by the computer processor of the mobile device, or alternatively by a base station computer processor in which the mobile device is in communication with.

Specifically, computer program code is provided, which is operable to receive temperature data from the temperature sensor, and to compare the recommended storage temperatures for the sample pills or capsules to the received temperature data, thereby determining compliance with the recommended storage temperatures. Further, the computer program code is operable to cause a service to play an audio file on the RFID-enabled mobile device comprising notification of the compliance or non-compliance with the recommended storage temperatures for the sample pills or capsules. Further, preferably, the computer program code is provided which is operable to inform the user of the time range out of recommended storage temperatures that damages or renders pills or capsules ineffective or dangerous for consumption.

Another frequent problem encountered by elderly or infirm users is the inability to properly orient the mobile device when capturing an image for optical recognition purposes, which is important for properly identifying the medication. To address this problem, in a further preferred embodiment, the present system comprises a gyroscopic detection device in communication with the computer processor of the mobile device, said gyroscopic detection device being operable to detect the 3 dimensional orientation of the mobile device (and thus the camera contained therein).

In addition, computer program code is provided, which operable to compare the detected 3 dimensional orientation of the mobile device to a predetermined proper orientation for the mobile device, and operable to cause a service to play an audio file on the RFID-enabled mobile device, the audio file comprising instructions concerning reorientation of the mobile device needed to correspond the detected orientation thereof to the predetermined proper orientation. The gyroscopic detection device, in conjunction with the software described above, thereby enables a user to properly orient the mobile device, as determined by the system administrator.

The programming necessary to effectuate the general functional steps/processes performed in connection with the present invention, as described in detail above, is relatively straight-forward and should be apparent to the relevant programming public. Accordingly, such programming is not attached hereto. Any particular programming, then, may be employed to effectuate the present invention without departing from the spirit and scope thereof.

Although focus has been given to wireless devices and communications and the advantages these technologies offer, the present invention is not limited to wireless devices, but rather may also be carried out using non-wireless communication devices, such as a processor-equipped telephone connected to a public switched telephone network (PSTN). An example of such a fixed line device would be a telephone equipped to receive digital information via a network where the audio file is stored in memory and when initiated by an RFID read event, is disseminated through a speaker, in the case of a ringtone, or through the earpiece in case of the voice message.

In addition, RFID technology also permits the recording of data. Thus, patient compliance data may be recorded. For example, when the patient reads the RIFD tag associated with a particular medicine, a date stamp may be associated with the occurrence and recorded. This record may be stored in the phones memory or sent as a file to a storage device or as a message to a caregiver. In this manner, information regarding how many times a patient has taken their medication may be recorded and communicated to the patient or appropriate caregiver or medical personnel.

In another embodiment, it is envisioned that the device and software of the current invention also comprises an alarm function, which provides an audible signal indicating to the user that it is time to take a specific drug or regime of drugs. The audible signal may be a ringtone, voice message, or other sound used for purposes of alerting an individual. In this regard, the current invention signals the patient at the appropriate time according to a preset dosing schedule. Recording the patient's acknowledgment of the alarm may be used as a means monitor the patient's compliance. Patient's acknowledgement may be recorded at the press of a button, or preferably, and recorded at the time the user scans proper medicine(s). This alarm function may be controlled remotely where the dosage schedule is pushed to the phone, or may be controlled locally by the patient.

RFID technology, for delivery of the medicine dosage, is but one example of a wireless technology for data delivery, but can be extended to any frequency in the electromagnetic spectrum. It should be understood that this invention is not limited to the particular embodiments disclosed, but it is intended to cover modifications within the spirit and scope of the present invention as defined by the appended claims.

Although specific embodiments of the present invention have been disclosed herein, those having ordinary skill in the art will understand that changes can be made to the specific embodiments without departing from the spirit and scope of the invention. Thus, the scope of the invention is not to be restricted to the specific embodiments. Furthermore, it is intended that the appended claims cover any and all such applications, modifications, and embodiments within the scope of the present invention.

What is claimed is:

1. A system for identifying medicine, and communicating dosage and intake instructions thereof to a patient via an RFID-enabled mobile device, said system comprising:
   (a) one or more RFID tags having a unique identifier associated therewith, the one or more RFID tags being adjacent to medicine and/or a medicine container, said medicine being in the form of pills and/or capsules;
   (b) an RFID-enabled mobile device comprising a computer processor, a wireless communications means, an RFID reader, a camera, and a non-transitory computer readable medium, all of which are in communication with one or more of each other; and
   (c) a subsystem operable to identify pills and capsules via optical recognition methods based on one or more of color, shape and size, associate one or more users with one or more pills and capsules, and transmit an audio file in the form of one or more of a ringtone, text message, one or more vibrations and/or a voice message associated with the unique identifier embodied on an RFID tag comprising identity of medicine and instructions related to medicine usage via a network to a RFID-enabled mobile device, said subsystem comprising computer application program code embodied on the non-transitory computer readable medium executable by the processor, said system for identifying medicine, and communicating dosage and intake instructions thereof to a patient via an RFID-enabled mobile device, said system comprising computer program code operable to:
      (i) generate, store and transmit a date stamp corresponding to the unique identifier when an RFID tag containing the unique identifier is read, and compare the date stamp to medicine dosage and intake instructions corresponding to the patient, so as to determine compliance therewith;
      (ii) receive an image of a sample pill or capsule from the camera and/or processor, generate a data set of optical characteristics of the pill or capsule based on the image, and compare the data set of optical characteristics of the sample pill or capsule to a database of known optical characteristics of known pills and capsules so as to determine identity of the sample pill or capsule;
      (iii) compare the identified sample pill or capsule, medicine dosage and intake instructions to patient medicine identity, dosage and intake requirements, so as to determine compliance therewith;
      (iv) cause a service to generate and play an audible and/or vibrational alarm so as to inform the user of the need to take the one or more medicines associated with the user, and record acknowledgement of the audible and/or vibrational alarm by the user, so as to determine compliance with medicine dosage and intake instructions; and
      (v) cause a service to play an audio and/or vibrational file on the RFID-enabled mobile device, said audio and/or vibrational file comprising identity of the sample pill or capsule, and instructions related to dosage and intake thereof.

2. The system for identifying medicine, and communicating dosage and intake instructions thereof to a patient via an RFID-enabled mobile device of claim 1, further comprising:
   a temperature sensor in communication with the computer processor,
   computer program code operable to receive temperature data from the temperature sensor, and compare recommended storage temperatures for the sample pills or capsules to the received temperature data so as to determine compliance therewith; and
   computer program code operable to cause a service to play an audio and/or vibrational file on the RFID-enabled mobile device, said audio file comprising notification of the compliance or non-compliance with recommended storage temperatures for the sample pills or capsules, and optionally time range out of recommended storage temperatures that damages or renders pills or capsules ineffective or dangerous for consumption.

3. The system for identifying medicine, and communicating dosage and intake instructions thereof to a patient via an RFID-enabled mobile device of claim 1, wherein the RFID-enabled mobile device is operable to communicate with an authorized mobile phone.

4. The system for identifying medicine, and communicating dosage and intake instructions thereof to a patient via an RFID-enabled mobile device of claim 1, wherein the RFID-enable mobile device is a mobile phone.

5. The system for identifying medicine, and communicating dosage and intake instructions thereof to a patient via an RFID-enabled mobile device of claim 1, further comprising:
   a gyroscopic detection device in communication with the computer processor, said gyroscopic detection device operable to detect the three dimensional orientation of the mobile device;
   computer program code operable to compare the detected three dimensional orientation of the mobile device to a predetermined proper orientation for the mobile device; and
   computer program code operable to cause a service to play an audio and/or vibrational file on the RFID-enabled mobile device, said audio and/or vibrational file comprising instructions concerning reorientation of the mobile device needed to correspond the detected orientation thereof to the predetermined proper orientation.

6. A system comprising:
   at least one RFID tag associated with a corresponding medicine and with at least one corresponding identifier, the at least one RFID tag placed adjacent to one of the medicine or a container containing the medicine;
   an RFID-enabled mobile device configured to:
      receive data representative of the at least one identifier corresponding to the at least one RFID tag when a reader of the RFID-enabled mobile device reads the at least one RFID tag,
      determine medication information associated with the at least one identifier corresponding to the at least one RFID tag, and
      generate user output corresponding to the determined medication information associated with the at least one identifier corresponding to the at least one RFID tag and
   a gyroscopic detection device to detect a three dimensional orientation of the RFID-enabled mobile device;
   wherein the RFID-enabled mobile device is further configured to:
      compare the detected three dimensional orientation of the mobile device to a predetermined proper orientation for the mobile device, and
      in response to a determination that the detected orientation of the mobile device does not match the predetermined proper orientation of the mobile device, generate orientation-related user output including instructions to cause re-orientation of the mobile device so that a subsequent detected orientation matches the predetermined proper orientation.

7. The system of claim 6, wherein the RFID-enabled mobile device configured to determine medication information associated with the at least one identifier corresponding to the at least one RFID tag is configured to:
identify from stored data records a data record corresponding to the at least one identifier, the identified data record including medicine dosage and intake instructions corresponding to a patient associated with the RFID-enabled mobile device and to the medicine associated with the at least one RFID tag.

8. The system of claim 6, wherein the RFID-enabled mobile device configured to generate the user output corresponding to the determined medication information is configured to generate one or more of: a ringtone, a text message, voice message, or vibration output.

9. The system of claim 6, wherein the RFID-enabled mobile device configured to generate user output corresponding to the determined medication information is configured to:
obtain customized one or more audio files relating to one or more of identity, dosage information, or intake instructions corresponding to a patient associated with the RFID-enabled mobile device and to the medicine associated with the at least one RFID tag.

10. The system of claim 6, further comprising:
a temperature sensor to measure temperature associated with one of the medicine or the container containing the medicine;
wherein the RFID-enabled mobile device is further configured to:
determine whether the measured temperature is in compliance with a recommended storage temperature for the medicine, and
generate temperature-related user output to notify one of compliance or non-compliance of the measured temperature with the recommended storage temperature for the medicine.

11. The system of claim 6, further comprising:
an image capture unit; and
an optical recognition subsystem configured to receive an image of the medicine captured by the image capture unit and to determine based on the captured image identity of the medicine.

12. The system of claim 11, wherein the identity of the medicine determined based on the captured image is compared to medicine identification data determined based on the at least one identifier to verify accuracy of the medicine identification data.

13. The system of claim 11, wherein the optical recognition subsystem configured to determine based on the captured image the identity of the medicine is configured to:
determine the identity of the medicine based on optical characteristics of the medicine determined from the captured image, the optical characteristics comprising one or more of: color of the medicine, shape of the medicine, or size of the medicine.

14. The system of claim 6, wherein the RFID-enabled mobile device comprises an RFID-enabled mobile phone.

15. The system of claim 6, wherein the at least one RFID tag includes an RFID tag printed with a medicine label, or an attachable RFID tag attached to the container or a cap of the container.

16. A method comprising:
receiving at an RFID-enabled mobile device data representative of at least one identifier corresponding to at least one RFID tag associated with a corresponding medicine, the at least one RFID tag placed adjacent to one of the medicine or a container containing the medicine;
determining based on the received data medication information associated with the at least one identifier corresponding to the at least one RFID tag;
generating user output corresponding to the determined medication information associated with the at least one identifier corresponding to the at least one RFID tag;
detecting with a gyroscopic detection device a three dimensional orientation of the RFID-enabled mobile device;
comparing the detected three dimensional orientation of the mobile device to a predetermined proper orientation for the mobile device; and
in response to a determination that the detected orientation of the mobile device does not match the predetermined proper orientation of the mobile device, generating orientation-related user output including instructions to cause re-orientation of the mobile device so that a subsequent detected orientation matches the predetermined proper orientation.

17. The method of claim 16, wherein determining medication information associated with the at least one identifier corresponding to the at least one RFID tag comprises:
identifying from stored data records a data record corresponding to the at least one identifier, the identified data record including medicine dosage and intake instructions corresponding to a patient associated with the RFID-enabled mobile device and to the medicine associated with the at least one RFID tag.

18. The method of claim 16, wherein generating the user output corresponding to the determined medication information comprises:
generating one or more of: a ringtone, a text message, voice message, or vibration output.

19. The method of claim 16, further comprising:
receiving an image of the medicine;
determining based on the image identity of the medicine; and
comparing the identity of the medicine determined based on the image to medicine identification data determined based on the at least one identifier to verify accuracy of the medicine identification data.

20. A system comprising:
at least one RFID tag associated with a corresponding medicine and with at least one corresponding identifier, the at least one RFID tag placed adjacent to one of the medicine or a container containing the medicine;
an RFID-enabled mobile device configured to:
receive data representative of the at least one identifier corresponding to the at least one RFID tag when a reader of the RFID-enabled mobile device reads the at least one RFID tag,
determine medication information associated with the at least one identifier corresponding to the at least one RFID tag, and
generate user output corresponding to the determined medication information associated with the at least one identifier corresponding to the at least one RFID tag;
an image capture unit; and
an optical recognition subsystem configured to receive an image of the medicine captured by the image capture unit and to determine identity of the medicine based on optical characteristics of the medicine determined from the captured image, the optical characteristics comprising one or more of: color of the medicine, shape of the medicine, or size of the medicine.

21. The system of claim 20, wherein the identity of the medicine determined based on the optical characteristics of the medicine determined from the captured image is compared to medicine identification data determined based on the at least one identifier to verify accuracy of the medicine identification data.

22. The system of claim 20, wherein the RFID-enabled mobile device configured to determine medication information associated with the at least one identifier corresponding to the at least one RFID tag is configured to:
identify from stored data records a data record corresponding to the at least one identifier, the identified data record including medicine dosage and intake instructions corresponding to a patient associated with the RFID-enabled mobile device and to the medicine associated with the at least one RFID tag.

23. The system of claim 20, wherein the RFID-enabled mobile device configured to generate user output corresponding to the determined medication information is configured to:
obtain customized one or more audio files relating to one or more of identity, dosage information, or intake instructions corresponding to a patient associated with the RFID-enabled mobile device and to the medicine associated with the at least one RFID tag.

24. The system of claim 20, further comprising:
a temperature sensor to measure temperature associated with one of the medicine or the container containing the medicine;
wherein the RFID-enabled mobile device is further configured to:
determine whether the measured temperature is in compliance with a recommended storage temperature for the medicine, and
generate temperature-related user output to notify one of compliance or non-compliance of the measured temperature with the recommended storage temperature for the medicine.

25. The system of claim 20, wherein the at least one RFID tag includes an RFID tag printed with a medicine label, or an attachable RFID tag attached to the container or a cap of the container.

26. A method comprising:
receiving data representative of at least one identifier corresponding to at least one RFID tag associated with a corresponding medicine, the at least one RFID tag placed adjacent to one of the medicine or a container containing the medicine;
determining based on the received data medication information associated with the at least one identifier corresponding to the at least one RFID tag;
generating user output corresponding to the determined medication information associated with the at least one identifier corresponding to the at least one RFID tag;
receiving an image of the medicine; and
determining identity of the medicine based on optical characteristics of the medicine determined from the received image of the medicine, the optical characteristics comprising one or more of: color of the medicine, shape of the medicine, or size of the medicine.

27. The method of claim 26, further comprising:
comparing the identity of the medicine determined based on the image to medicine identification data determined based on the at least one identifier to verify accuracy of the medicine identification data.

28. The method of claim 26, wherein determining medication information associated with the at least one identifier corresponding to the at least one RFID tag comprises:
identifying from stored data records a data record corresponding to the at least one identifier, the identified data record including medicine dosage and intake instructions corresponding to a patient associated with the RFID-enabled mobile device and to the medicine associated with the at least one RFID tag.

29. The method of claim 26, wherein generating the user output corresponding to the determined medication information comprises:
generating one or more of: a ringtone, a text message, voice message, or vibration output.

* * * * *